United States Patent
Heyman et al.

(10) Patent No.: US 6,517,502 B2
(45) Date of Patent: Feb. 11, 2003

(54) ORTHOTIC DEVICE AN METHODS FOR LIMITING EXPANSION OF A PATIENT'S CHEST

(75) Inventors: Arnold M. Heyman, Los Angeles, CA (US); Tom Heinz, Flintridge, CA (US)

(73) Assignee: Biocybernetics International, Pasadena, CA (US)

( * ) Notice: Subject to any disclaimer, the term of this patent is extended or adjusted under 35 U.S.C. 154(b) by 79 days.

(21) Appl. No.: 09/760,707

(22) Filed: Jan. 17, 2001

(65) Prior Publication Data

US 2001/0034498 A1 Oct. 25, 2001

Related U.S. Application Data

(60) Provisional application No. 60/180,626, filed on Feb. 7, 2000.

(51) Int. Cl.$^7$ .................................................. A61F 5/00
(52) U.S. Cl. .............................. 602/5; 602/19; 128/876; 128/96.1
(58) Field of Search ...................... 602/5, 19; 128/95.1, 128/96.1, 98.1, 876; 2/310–312

(56) References Cited

U.S. PATENT DOCUMENTS

| | | |
|---|---|---|
| 232,420 A | 9/1880 | Smith |
| 321,146 A | 6/1885 | Spencer |
| 571,749 A | 11/1896 | Colton |
| 746,563 A | 12/1903 | McMahon |
| 787,894 A | 4/1905 | Colton |
| 894,066 A | 7/1908 | Scarpa |
| 1,469,661 A | 10/1923 | Migita |
| 1,530,713 A | 3/1925 | Clark |
| 2,036,484 A | 4/1936 | Le May |
| 2,100,964 A | 11/1937 | Kendrick |
| 2,219,475 A | 10/1940 | Flaherty |
| 4,508,110 A | 4/1985 | Modglin |
| 4,641,642 A * | 2/1987 | Williams, Jr. ............... 128/96.1 |
| 5,399,151 A | 3/1995 | Smith |
| 5,437,617 A * | 8/1995 | Heinz et al. ................... 602/19 |
| 5,499,965 A * | 3/1996 | Sanchez ..................... 128/96.1 |
| 5,599,287 A | 2/1997 | Beczak, Sr. et al. |
| 5,843,008 A * | 12/1998 | Gerhard .......................... 602/5 |
| 6,213,968 B1 * | 4/2001 | Heinz et al. ................... 602/19 |

FOREIGN PATENT DOCUMENTS

KR        20-0146563        2/1999

* cited by examiner

Primary Examiner—Michael A. Brown
Assistant Examiner—Quang D. Thanh
(74) Attorney, Agent, or Firm—Arent Fox Kintner Plotkin & Kahn, PLLC

(57) ABSTRACT

An orthotic device includes a pair of panel members and a mechanical advantage device that bridges the pair of panel members together to form a belt with two free end portions detachably connectable to each other. The mechanical advantage device has a drawstring element that causes the mechanical advantage device to move from an expanded state wherein the bridged end portions are disposed apart from one another to a contracted state wherein the respective bridged end portions are drawn towards each other. Methods are also described. One method includes the steps of donning the orthotic device about the patient's chest, connecting the free end portions of the orthotic device together with the mechanical advantage device in the expanded state, and pulling the drawstring element a selected distance to move the mechanical advantage device from the expanded state to the contracted state for a desired level of tightening.

17 Claims, 7 Drawing Sheets

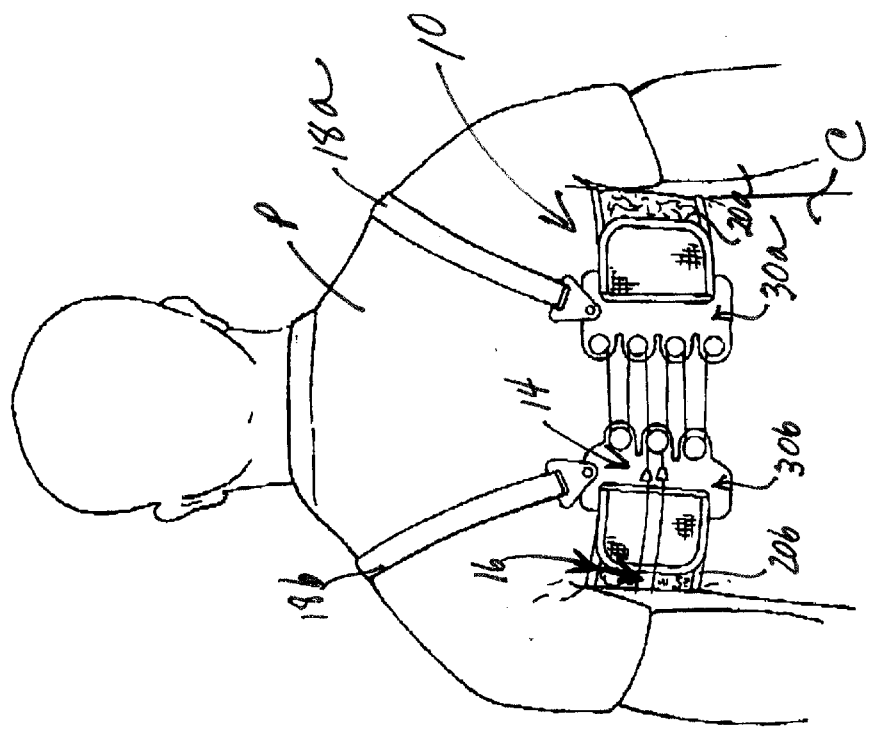
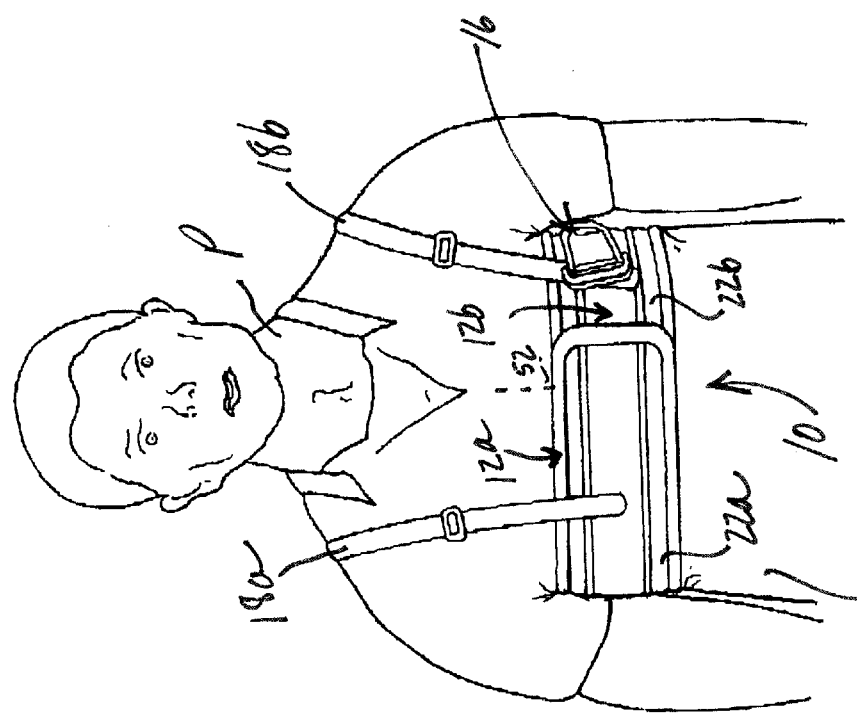

ORTHOTIC DEVICE AN METHODS FOR LIMITING EXPANSION OF A PATIENT'S CHEST

This application claims the benefit of U.S. provisional application No. 60/180,626 filed Feb. 7, 2000

FIELD OF THE INVENTION

The invention is directed to an orthotic device and methods for limiting expansion of a patient's chest. The inventions are particularly useful for minimizing chest pain in the patient's chest during recovery of a surgically repaired split sternum.

BACKGROUND OF THE INVENTION

Every year, many patients undergo surgery, such as heart surgery, that requires entry through the patient's chest. Often, to enter the patient's chest, the surgeon dissects the patient's sternum, sometimes referred to as the breastbone, to gain access to the patient's chest cavity. Typically, the sternum is split along its vertical midline so that the front of the rib cage can be spread open to create access to the patient's chest cavity. Upon completion of the surgery, the adjacent ends of the split sternum are usually wired together to close the opening into the chest cavity.

Typically, the patient is encouraged, particularly in post-op physical therapy, to breath deeply. However, deep breathing causes the patient's chest to expand when inhaling. Such expansion tends to pull the wired adjacent sides of the sternum apart causing pain to the patient. Such pain causes a reluctance on the patient's part to comply with post-op physical therapy treatment.

Also, natural bodily movements such as sitting up, standing up and walking tend to pull apart the wired adjacent sides of the surgically repaired split sternum. These ordinary bodily movements also cause the patient pain.

Further, normal bodily functions such as coughing, sneezing, defecating and belching cause chest wall expansion which, in turn, generates pain for the patient recovering from surgery through the chest. This pain is quite acute because of the sudden upwardly movement of the patient's diaphragm. This sudden upwardly movement of the diaphragm causes a sudden increase intra-abdominal pressure which causes significant expansion of the entire rib cage. Significant expansion of the entire rib cage pulls the wired adjacent sides of the surgically repaired sternum apart causing the patient significant pain.

OBJECTS AND SUMMARY OF THE INVENTION

It is an object of the invention to provide an orthotic device and methods that limit expansion of a patient's chest while the patient is recovering from a surgically repaired split sternum.

Another object of the invention is to provide an orthotic device and methods for limiting expansion of a patient's chest of a patient recovering from a surgically repaired split sternum in order to minimize pain during deep breathing, sitting up, standing up, walking, coughing, sneezing, belching and/or defecating.

Yet another object of the invention is to provide an orthotic device for limiting expansion of a patient's chest of a patient recovering from a surgically repaired split sternum that fits well on the patient.

Accordingly, an orthotic device and methods for limiting expansion of a patient's chest are hereinafter described. The orthotic device of the invention is sized and adapted to be donned around the patient's chest. The orthotic device of the invention includes a pair of panel members fabricated from a flexible material and a mechanical advantage device. The pair of panel members are bridged at respective ends portions to each other by the mechanical advantage device to form a belt with two free end portions detachably connectable to each other. The mechanical advantage device has a drawstring element operably connected to and extending from the mechanical advantage device for causing the mechanical advantage device to move from an expanded state to a contracted state. In the expanded state, the respective bridge end portions are disposed apart from one another. In the contracted state, the respective bridge end portions are drawn towards each other. The orthotic device is donned about the patient's chest with free end portions in front being connected together with the mechanical advantage device in the expanded state. Pulling the drawstring element a selected distance moves the mechanical advantage device from the expanded state to the contracted state. The selected distance is commensurate with a desired level of tightening of the orthotic device about the patient's chest to limit expansion of the patient's chest.

Another embodiment of the invention is a method for limiting the expansion of the patient's chest. One step includes providing the orthotic device described above. Another step is donning the orthotic device about the patient's chest. Another step is connecting the free end portions of the orthotic device together while the mechanical advantage device is in the expanded state. Another step is pulling the drawstring element a selected distance thereby moving the mechanical advantage device from the expanded state to the contracted state.

BRIEF DESCRIPTION OF THE DRAWINGS

FIGS. 2A and 2B are front and rear elevational views respectively of the orthotic device of the invention donned by a patient around the patient's chest with a mechanical advantage device shown in an expanded state.

DETAILED DESCRIPTION OF THE INVENTION

Figure 1:
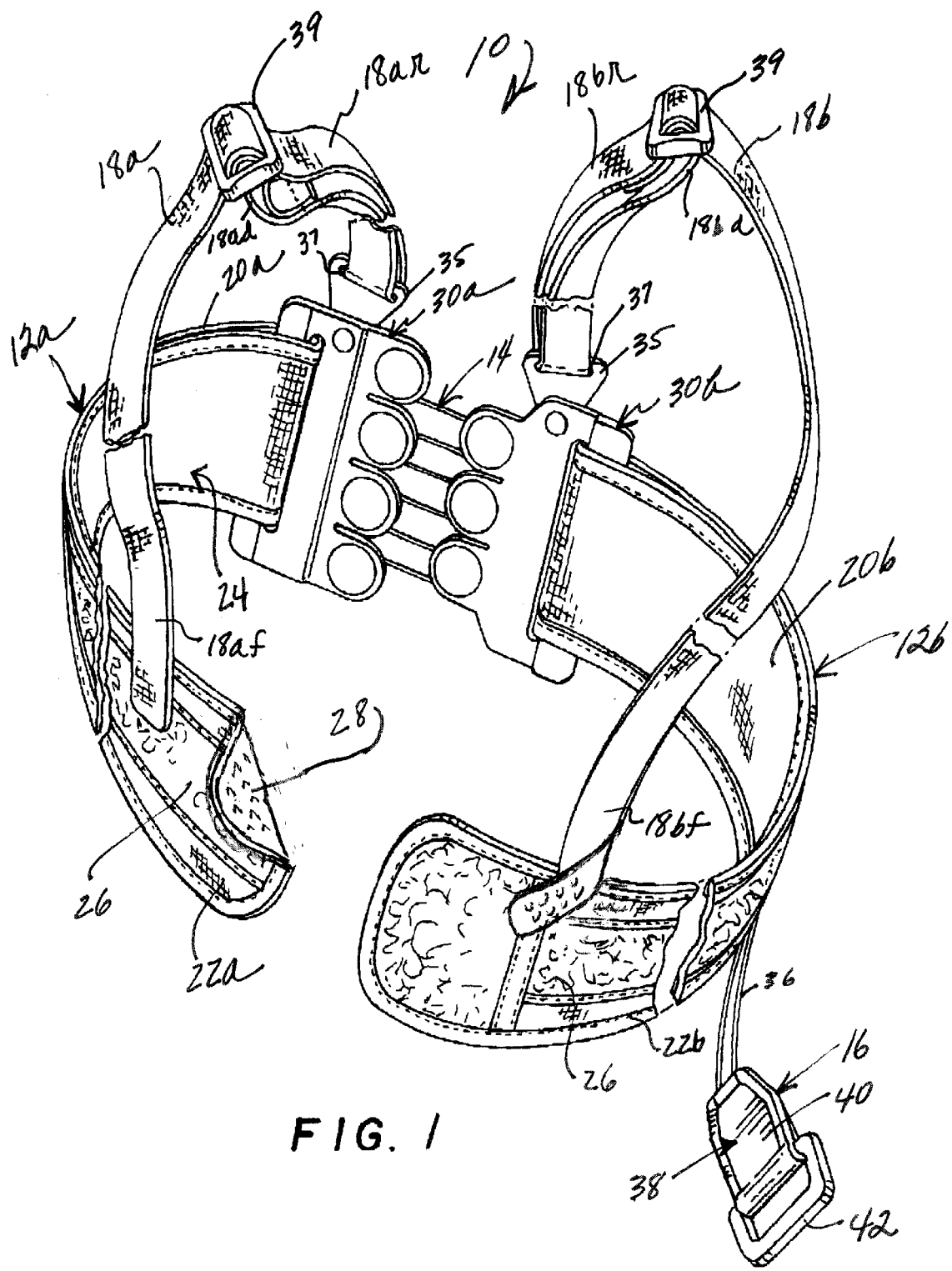
FIG. 1 is a perspective view of an orthotic device of the invention.

An orthotic device 10 of the invention that is used for limiting expansion of a chest C of a patient P is introduced in FIGS. 1–6. The orthotic device 10 of the invention includes a pair of panel members 12a and 12b, a mechanical advantage device 14, a drawstring element 16 and a pair of shoulder straps 18a and 18b. The pair of panel members 12a and 12b are fabricated from a flexible material such as nylon or nylon mesh or suitable fabric material. Each one of the panel members 12a and 12b has a first end portion 20a and 20b respectively and a free end portion 22a and 22b respectively. The free end portions 22a and 22b are detachably connectable to each other in front of the patient's body.

Figure 3B:
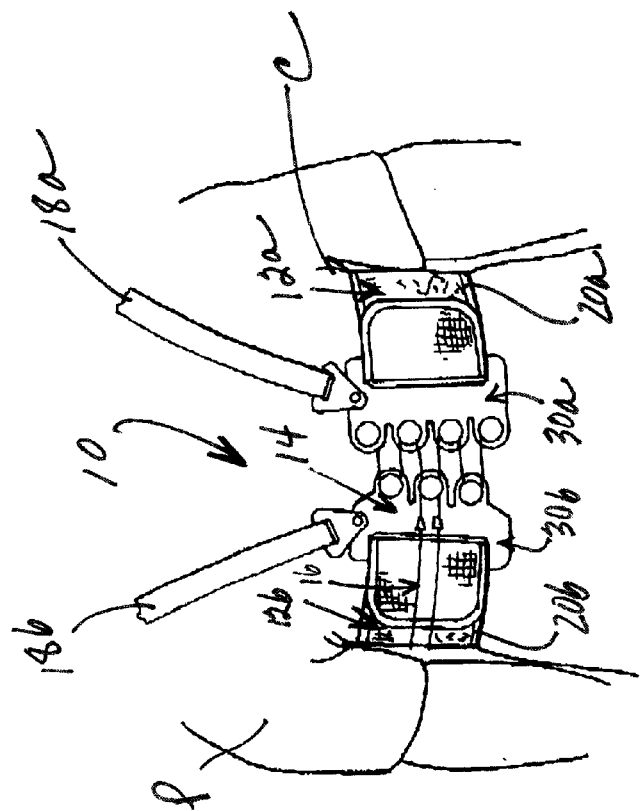
FIGS. 3A and 3B are front and rear elevational views respectively of the orthotic device of the invention showing the mechanical advantage device in the contracted state.

As shown in FIGS. 1, 2B and 3B, the mechanical advantage device 14 bridges together the respective ones of the first end portions 20a and 20b to form a belt 24 having bridged first end portions 20a and 20b. Also, the drawstring element 16 is operably connected to and extends from the mechanical advantage device 14. The drawstring element 16 causes the mechanical advantage device 14 to move from an expanded state shown in FIG. 2B to a contracted state shown in FIG. 3B. In the expanded state (FIG. 2B), the respective bridged first end portions 20a and 20b are disposed apart from one another. In the contracted state (FIG. 3B), the respective bridged first end portions 20a and 20b are drawn towards each other.

As discussed in more detail below, the shoulder strap 18a interconnects one end of the mechanical advantage device 14 and the free end portion 22a. Also, the shoulder strap 18b interconnects an opposite end of the mechanical advantage device 14 and the free end portion 22b of the panel member 12b. In other words, respective ones of the pair of shoulder straps 18a and 18b interconnect the mechanical advantage device and the free end portions 22a and 22b. As best shown in FIGS. 2A–3B, the pair of shoulder straps 18a and 18b are positioned over the shoulders of patient P in order to retain the orthotic device 10 of the invention about the patient's chest C in a desired vertical position when the mechanical advantage device 14 is in the expanded state.

Figure 3A:
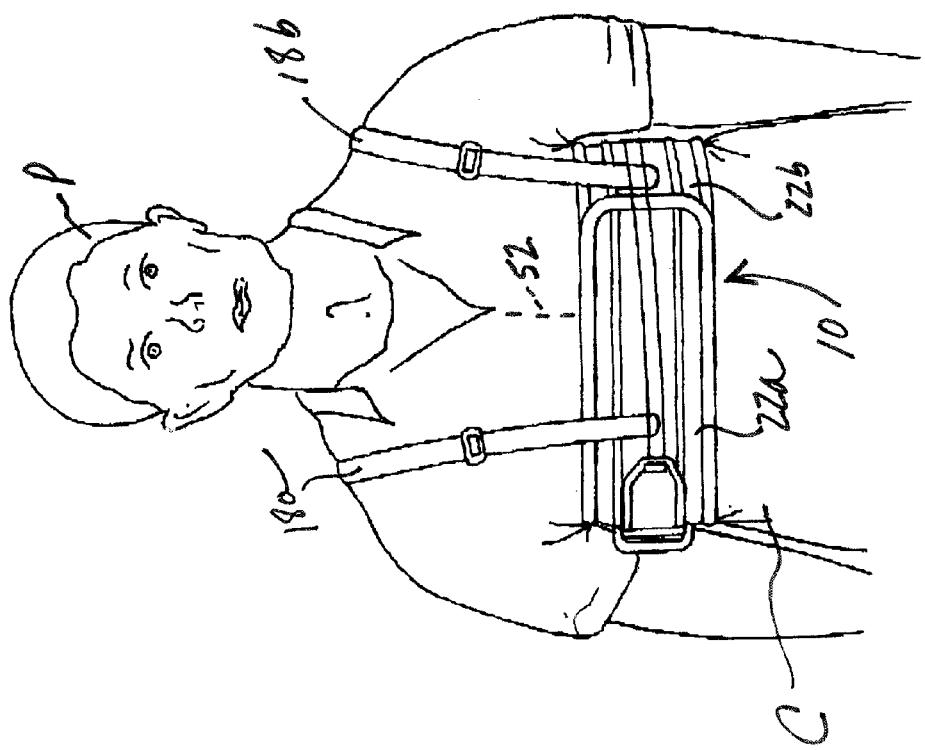
Figure 5:
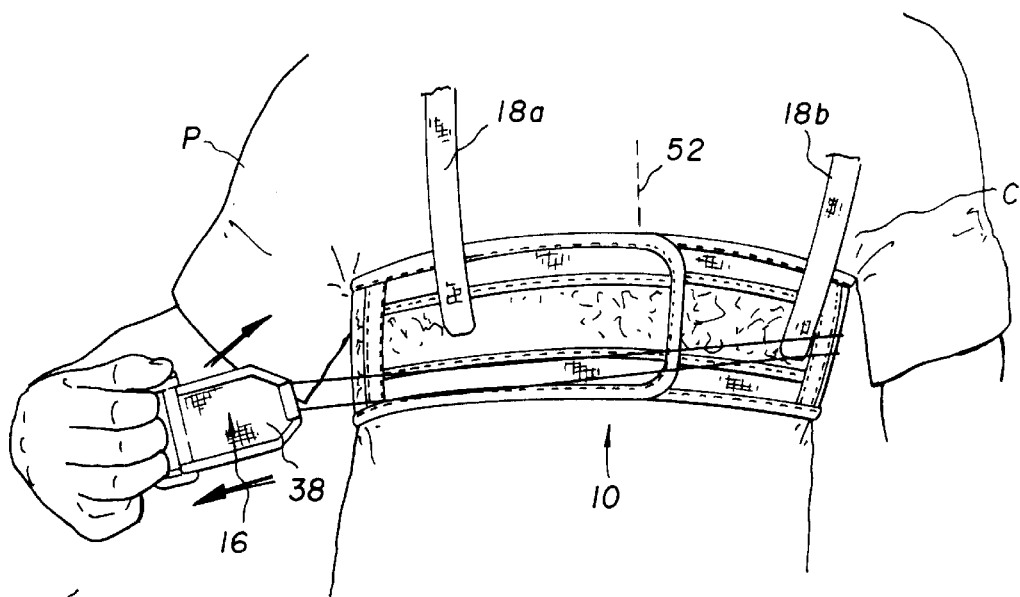
FIG. 5 is a front elevational view of the patient pulling the drawstring element of the orthotic device in order to move the mechanical advantage device from the expanded state to a contracted state.
Figure 6:
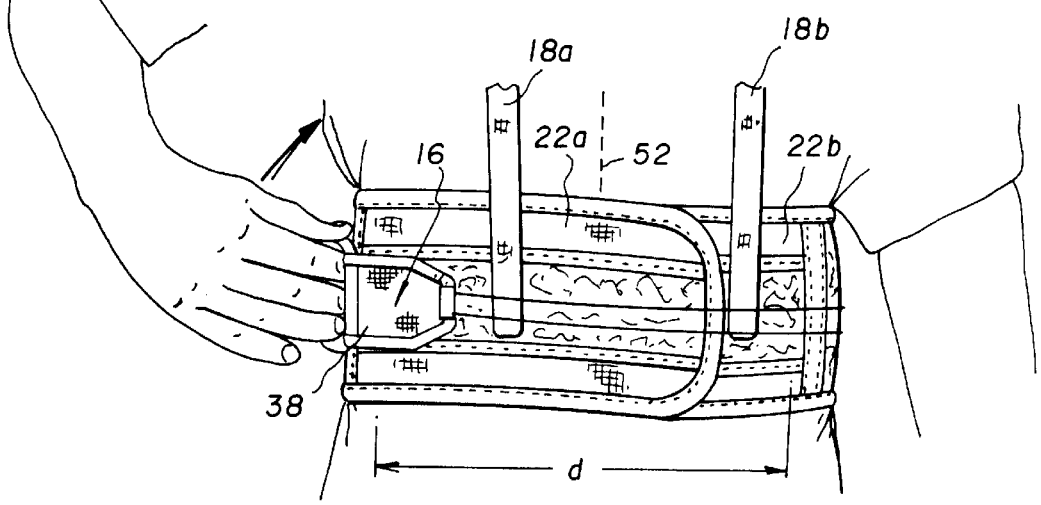
FIG. 6 is a partial front elevational view of the patient releasably connecting the drawstring element of the orthotic device of the invention to retain the mechanical advantage device in the contracted state.

In FIGS. 2A and 2B, the orthotic device 10 of the invention is donned about the patient's chest C with the free end portions 22a and 22b being releasably connected together and with the mechanical advantage device 14 being in the expanded state. As shown sequentially in FIGS. 4–6 and discussed in more detail below, the patient P pulls the drawstring element 16 by one hand a selected distance "d" (FIG. 6). Pulling the drawstring element 16 the selected distance "d" moves the mechanical advantage device 14 from the expanded state (FIGS. 2A and 2B) to the contracted state (FIGS. 3A and 3B). The selected distance "d" is commensurate with a desired level of tightening of the orthotic device 10 of the invention about the patient's chest C to limit expansion of the patient's chest C.

The orthotic device 10 of the invention includes the use of hook-and-loop material. It is preferred that certain sections as described below of the orthotic device 10 of the invention has hooked portions of the hook-and-loop material while other sections of the orthotic device 10 of the invention has looped portions of the hook-and-loop material. However, one of ordinary skill in the art would appreciate that the hook portions can be changed to the loop portions while, correspondingly, the loop portions can be changed to the hook portions. As a result, as hereinafter described, the use of the hook-and-loop material is used by way of example only and selected ones of the loop portions or the hook portions are chosen as a mere design choice. Further, one of ordinary skill in the art would appreciate that other devices or structures can be used to achieve the purpose of the hook-and-loop material as provided herein.

In FIG. 1, each one of the pair of panel members 12a and 12b includes loop material 26 that is attached exteriorly to at least the free end portions 22a and 22b. By way of example only, the free end portion 22a also includes hook material 28 that is attached interiorly thereof. A skilled artisan would appreciate that the hook material 28 attached interiorly to the free end portion 22a is used to detachably connect the free end portion 22a to the free end portion 22b, as shown in FIGS. 2A, 3A, and 4–6, which includes loop material.

Figure 7:
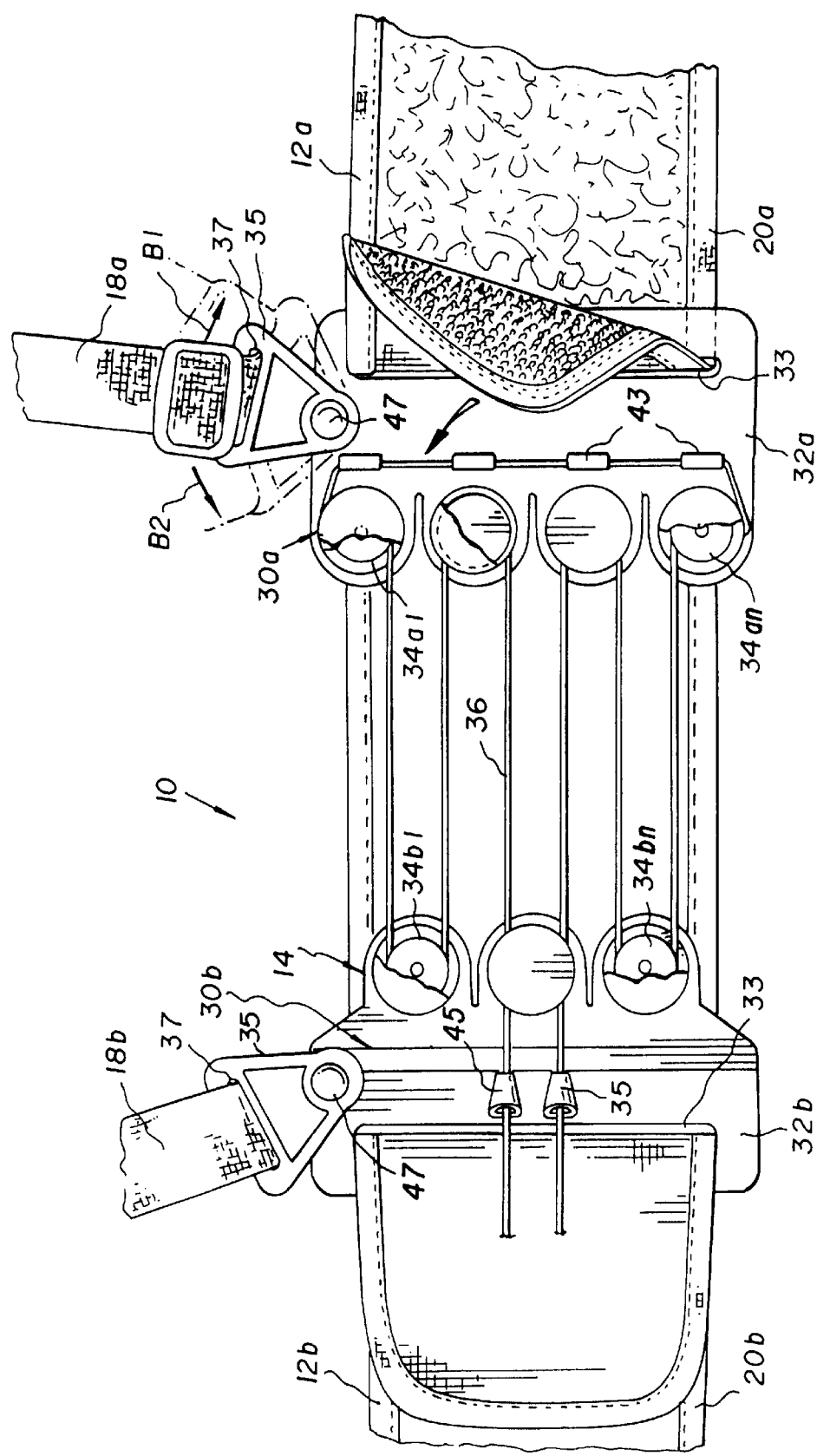
FIG. 7 is a front elevational view of the mechanical advantage device detachably connected to bridged first end portions of the orthotic device.

As best shown in FIG. 7, the mechanical advantage device 14 includes two pulley banks 30a and 30b. Each pulley bank 30a and 30b has a base member 32a and 32b respectively and a plurality of pulleys 34a1–34an and 34b1–34bn which are rotatably connected to the respective base members 32a and 32b. As best shown in FIGS. 1 and 7, the drawstring element 16 includes an endless loop drawstring 36 and a handle 38. The handle 38 is connected to a segment of the endless loop drawstring 36 while another segment of the endless loop drawstring 36 is operably connected to the mechanical advantage device 14. As illustrated in FIG. 7, the endless loop drawstring 36 is interlaced and looped around opposing pulleys 34a1–34an and 34b1–34bn on the opposing pulley banks 30a and 30b. Also, a section of the endless loop drawstring 36 is threaded through hollow tubular guides 43 positioned adjacent to and aligned in parallel with the alignment of the pulleys 34a1–34an on the base member 32a. Correspondingly, separate sections of the endless loop drawstring 36 is threaded through respective ones of hollow conically-shaped guides 45 positioned adjacent to the pulleys 34b1–34bn on the base member 32b to guide the endless loop drawstring 36 between the pulleys and the free end portions 20a and 20b on the front of the orthotic device 10 of the invention.

Figure 4:
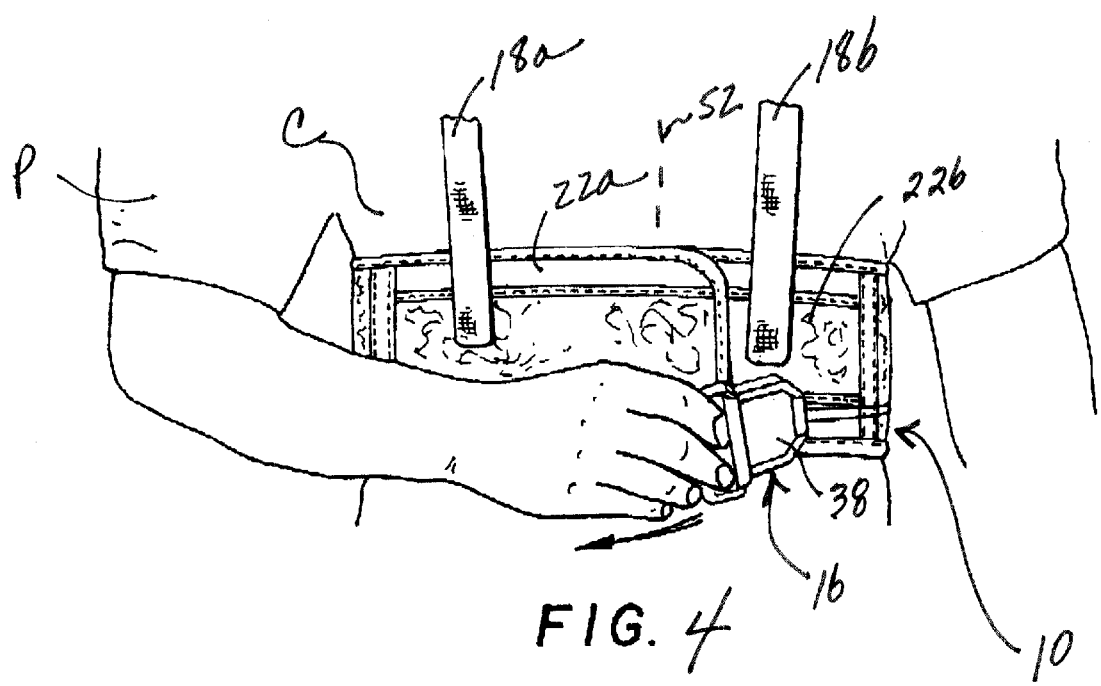
FIG. 4 is a partial front elevational view of the patient preparing to pull a drawstring element of the orthotic device of the invention while the mechanical advantage device is in the expanded state.

As shown in FIG. 1, the handle 38 has a tab portion 40 fabricated from hook-and-loop material and has a ring portion 42 which is connected to the tab portion 40. Preferably, the ring portion 42 is fabricated from a stiff material such as metal or plastic. The ring portion 42 is designed to be grasped by the patient's hand as shown in FIGS. 4–6. The tab portion 40 is appropriately fabricated from the hook portion of the hook-and-loop material so that the handle 38 can be releasably and selectively connected to either one of the two free end portions 22a and 22b of the pair of panel members 12a and 12b respectively.

With reference to FIG. 7, respective ones of the pulley banks 30a and 30b are detachably connected to the bridged first end portions 20a and 20b at respective base members 32a and 32b. Each base member 32a and 32b has an opening 33 formed therethrough that extends substantially parallel with the alignment of the pulleys 34a1–34an and 34b1–34bn respectively. Each opening 33 is sized to receive a respective one of the bridged first end portions 20a and 20b of the panel members 12a and 12b so that the bridged end portion received in the opening 33 can be folded back and releasably connected to itself. Although not by way of limitation, each one of the bridged first end portions 20a and 20b includes hook-and-loop material for releasably connecting to itself. One of ordinary skill in the art would appreciate that other means are available such as snaps which can be used to releasably connect the bridged first end portions 20a and 20b to themselves.

Also, as shown in FIG. 7, the orthotic device 10 of the invention includes a pair of fasteners 35. Each fastener 35 is interconnected to and between a respective one of the base members 32a and 32b and a respective one of the shoulder straps 18a and 18b. Each fastener 35 is pivotably connected to a respective one of the base members 32a and 32b and pivots about a fastening pin 47 as shown by arrows B1 and B2 in FIG. 7. A skilled artisan would appreciate that other types of fasteners are available to interconnect the respective shoulder straps and the base members.

Again, with reference to FIG. 1, each strap 18a and 18b has a rear end strap portion 18ar and 18br and a front end strap portion 18af and 18bf. Each fastener 35 has a slot 37 formed therethrough. Each slot 37 is sized to receive the rear end strap portion 18ar or 18i br of a respective strap 18a or 18b so that the rear end strap portion 18ar or 18br of the straps 18a and 18b respectively loops through the respective fasteners 35. The front end strap portion 18af and 18bf of each strap 18a and 18b is adapted for releasable connection to a respective one of the free end portions 22a and 22b of the panel members 12a and 12b respectively. Preferably, each front end strap portion 18af and 18bf of respective straps 18a and 18b includes hook-and-loop material. As best shown in FIG. 1, although not by way of limitation, the front end strap portion 18bf, for example, includes the hook portion of the hook-and-loop material so that it could be releasably connected to the loop portion of the free end portion 22b.

Also, the orthotic device 10 of the invention includes a pair of adjustor elements 39. As is well known in the art, each adjustor element 39 is fixedly connected to a respective distal end 18ad and 18bd of the rear end portion 18ar and 18br of respective straps 18a and 18b and is slidably connected to the respective straps 18a and 18b between the respective distal end 18ad and 18bd and the respective front end strap portion 18af and 18bf. Again, as is known in the art, the adjustor element 39 is slidable along the respective strap 18a or a18b for adjusting the belt 24 at a desired vertical position about the patient's chest C as shown in FIGS. 2A–6. Such adjustor elements 39 render each one of the pair of shoulder straps 18a and 18b adjustable.

Many of the features of the orthotic device 10 of the invention are disclosed in U.S. application Ser. No. 09/334, 649 filed Jun. 17, 1999, which is incorporated herein by reference for all purposes.

With reference to FIGS. 2A–6, a method of the invention for limiting expansion of the patient's chest is illustrated. The method includes providing an orthotic device such as the one described above. In FIG. 2A, the orthotic device 10 is donned about the patient's chest C. The free end portions 22a and 22b of the orthotic device 10 are connected together (FIG. 2A) while the mechanical advantage device 14 is in the expanded state (FIG. 2B). As sequentially shown in FIGS. 4–6, the drawstring element 16 is pulled the selected distance "d" (FIG. 6). Pulling the drawstring element 16 the selected distance "d" moves the mechanical advantage device from its expanded state (FIG. 2B) to its contracted state. (FIG. 3B). The selected distance "d" is commensurate with a desire level of tightening of the orthotic device 10 about the patient's chest C to limit the expansion of the patient's chest.

In FIG. 4, the patient P grabs the drawstring element 16 with one hand when the mechanical advantage device 14 is in its expanded state (FIG. 2B). The patient P then pulls the drawstring element 16 the selected distance "d" to move the mechanical advantage device to the contracted state (FIG. 3B). As shown in FIG. 6, once the patient P pulls the drawstring to the selected distance "d", the patient P releasably connects the drawstring element 16 to the other first free end portion 22a while the mechanical advantage device 14 is in its contracted state (FIG. 3B). One of ordinary skill in the art would comprehend that releasably connecting the drawstring element 16 to the other first free end portion 22a retains the mechanical advantage device 14 in its contracted state.

In FIG. 4, the drawstring element 16 is releasably connected to the free end portion 22b when the mechanical advantage device 14 is in its expanded state and before the patient P grabs the drawstring element 16. Thus, after the patient P grabs the drawstring element 16, the patient P disconnects the releasably connected drawstring element 16 from the free end portion 22b after grabbing the drawstring element 16.

Note that the handle 38 is selectably and releasably connected to either one of the two free end portions 22a and 22b of the pair of panel members 12a and 12b, respectively. Thus, it is possible that, depending on the size of the patient and the size of the orthotic device, the handle 38 can be releasably connected to the other free end portion 22a when the patient P grabs the drawstring element 16.

In any regard, performing the steps for the method of the invention for limiting expansion of a patient's chest can be achieved using only one hand of the patient P. Furthermore, the patient P can pull the drawstring element 16 at his/her discretion. As a result, when the patient P determines a cough or sneeze is forthcoming, the patient P can immediately move the orthotic device through use of the handle into its contracted state to limit chest expansion and mitigating chest pain upon coughing or sneezing and because a mechanical advantage device is used, the patient expends minimal effort to gain selective tightening of the orthotic device about the patient's chest.

Another method of the invention mitigates chest pain in the patient's chest. Chest pain typically results from expansion of a surgically repaired split sternum 52 illustrated by a dashed line in FIGS. 2A, 3A and 4–6. Mitigating the chest pain occurs by limiting chest expansion as described above.

Furthermore, the orthotic device of the invention fabricated from a flexible material fits well on the patient. Thus, the orthotic device of the invention is worn comfortably by the patient until the time when it must be tightened around the chest to mitigate pain as described above.

Figure 8:
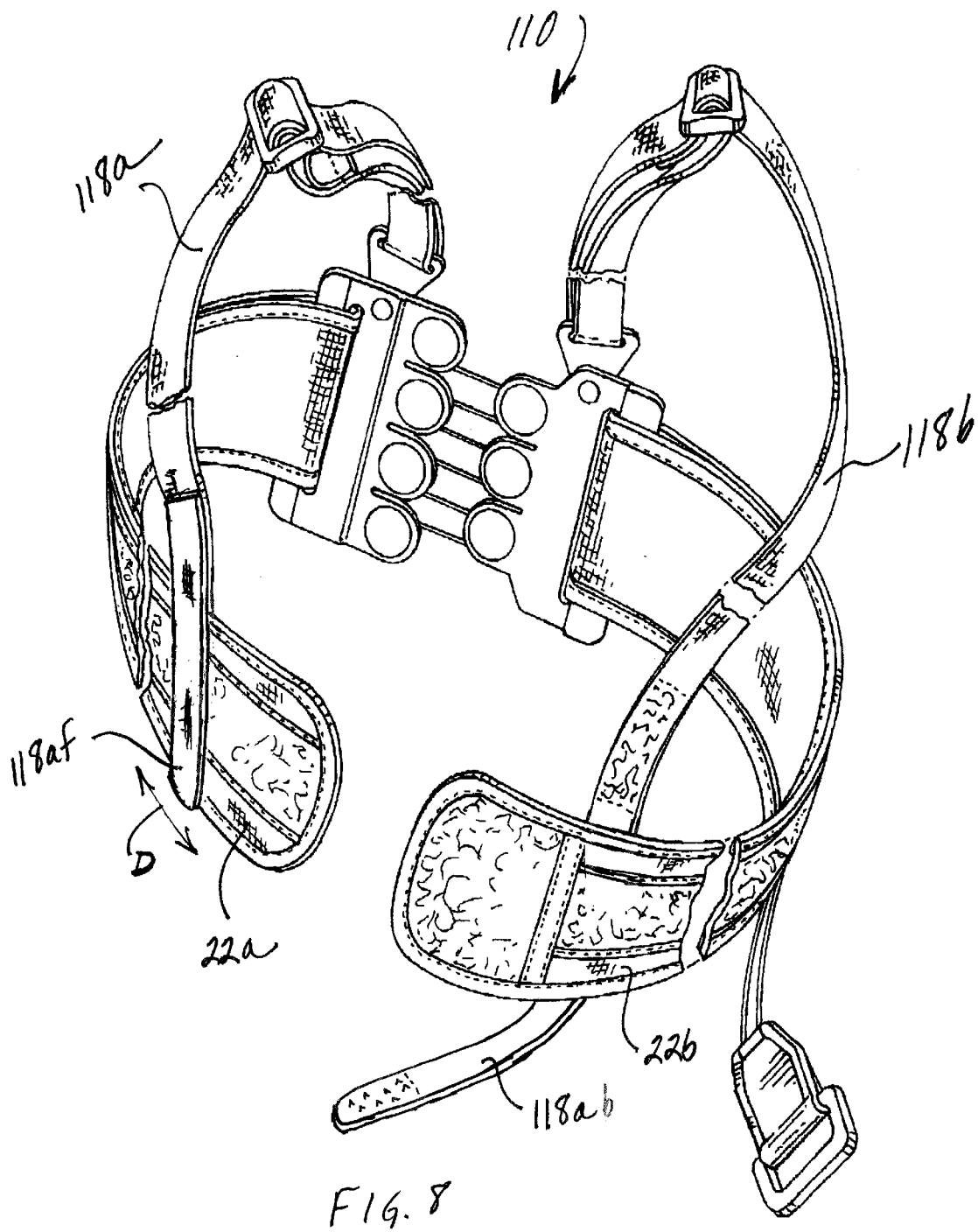
FIG. 8 is a perspective view of a second exemplary embodiment of the orthotic device of the invention having a pair of elongated shoulder straps for forming releasably connected strap loops about the orthotic device.

A second exemplary embodiment of an orthotic device 110 of the invention is illustrated in FIG. 8. The orthotic device 110 of the invention is similar to the one described above. Shoulder straps 118a and 118b are lengthened relative to the ones shown in the orthotic device 10 of the invention. Each shoulder strap 118a and 118b has a front end strap portion 118af and 118bf respectively which is sized and adapted for being releasably connected to itself by using, for example, hook and loop material. Each front end strap portion 118af and 118bf is particularly sized to extend behind and bend about a respective free end portion 22a and 22b of the orthotic device 110 in order to connect to itself to form a strap loop about the orthotic device 110. The strap loop is primarily fabricated from a fabric material that enables it is slide along the respective one of the free end portions 22a and 22b. The strap loop can be slid by the patient in the directions shown by the double-headed arrow D along the free end portions so as to avoid interference with releasably connecting the handle 38 anywhere along the free end portions 22a and 22b.

One of ordinary skill in the art would appreciate that changes may be made to the invention without departing from the inventive concepts described herein. It is understood, therefore, that the invention is not limited to the particular embodiments disclosed but is intended to encompass any modifications which are within the scope and spirit of the invention.

What is claimed is:

1. A method for limiting expansion of a patient's chest, the method comprising the steps of:

providing an orthotic device sized and adapted to be donned around the patient's chest, the orthotic device having a pair of panel members fabricated from a flexible material and a mechanical advantage device, the pair of panel members bridged at respective end portions to each other by the mechanical advantage device to form a belt with two free end portions detachably connectable to each other, the mechanical advantage device having a drawstring element operably connected to and extending from the mechanical advantage device for causing the mechanical advantage device to move from an expanded state wherein the respective bridged end portions are disposed apart from one another to a contracted state wherein the respective bridged end portions are drawn towards each other;

donning the orthotic device about the patient's chest;

connecting the free end portions of the orthotic device together while the mechanical advantage device is in the expanded state; and pulling the drawstring element a selected distance thereby moving the mechanical advantage device from the expanded state to the contracted state, the selected distance being commensurate with a desired level of tightening of the orthotic device about the patient's chest to limit the expansion of the patient's chest.

2. A method according to claim 1, further comprising the steps of grabbing the drawstring element releasably connected to one free end portion when the mechanical advantage device is in the expanded state, pulling the drawstring element the selected distance thereby moving the mechanical advantage device to the contracted state and releasably connecting the drawstring element to the other free end portion while the mechanical advantage device is in the contracted state.

3. A method according to claim 2, wherein releasably connecting the drawstring element to the other free end portion retains the mechanical advantage device in the contracted state.

4. A method according to claim 2, further comprising the step of releasably connecting the drawstring element to the one first free end portion when the mechanical advantage device is in the expanded state and before the step of grabbing the drawstring element.

5. A method according to claim 4, further comprising the step of disconnecting the releasably connected drawstring element from the one free end portion after the step of grabbing the drawstring element.

6. A method according to claim 1, further comprising the step of providing the drawstring element with an endless loop drawstring and a handle connected to a segment of the endless loop drawstring while another segment of the endless loop drawstring is operably connected to the mechanical advantage device.

7. A method according to claim 6, further comprising the step of providing the handle that is selectably and releasably connected to either one of the two free end portions of the pair of panel members.

8. A method according to claim 7, further comprising the steps of grabbing the handle releasably connected to the orthotic device when the mechanical advantage device is in the expanded state, disconnecting the releasably connected handle from the orthotic device, pulling the handle the selected distance thereby moving the mechanical advantage device to the contracted state and releasably connecting the handle to the orthotic device while the mechanical advantage device is in the contracted state.

9. A method according to claim 8, wherein the steps of grabbing the handle, disconnecting the releasably connected handle, pulling the handle and releasably connecting the handle are achieved using one hand of the patient.

10. A method according to claim 1, further comprising the step of providing each one of the pair of panel members with hook-and-loop material attached exteriorly to at least respective ones of the free end portions.

11. A method according to claim 10, further comprising the step of providing the drawstring element with a handle having a tab portion fabricated from hook-and-loop material and a ring portion connected to the handle portion and fabricated from a stiff material.

12. A method according to claim 1, further comprising the step of providing the mechanical advantage device with two pulley banks, each pulley bank having a base member and a plurality of pulleys rotatably connected to the base member.

13. A method according to claim 12, further comprising the step of providing respective ones of the pulley banks so that the pulley banks are detachably connected to the bridged end portions of the panel members.

14. A method according to claim 1, further comprising the step of providing the orthotic device with a pair of shoulder straps, each strap interconnecting the bridged end portion and the free end portion of each respective panel member.

15. A method according to claim 14, further comprising the step of providing each one of the pair of shoulder straps as being adjustable.

16. A method according to claim 1, wherein the step of pulling the drawstring element occurs at discretion of the patient.

17. A method for mitigating chest pain in a patient's chest resulting from expansion of a surgically repaired split sternum by limiting chest expansion, the method comprising the steps of:

providing an orthotic device sized and adapted to be donned around the patient's chest, the orthotic device having a pair of panel members fabricated from a flexible material and a mechanical advantage device, the pair of panel members bridged at respective end portions to each other by the mechanical advantage device to form a belt with two free end portions detachably connectable to each other, the mechanical advantage device having a drawstring element operably connected to and extending from the mechanical advantage device for causing the mechanical advantage device to move from an expanded state wherein the respective bridged end portions are disposed apart from one another to a contracted state wherein the respective bridged end portions are drawn towards each other;

donning the orthotic device about the patient's chest;

connecting the free end portions of the orthotic device together while the mechanical advantage device is in the expanded state; and pulling the drawstring element a selected distance thereby moving the mechanical advantage device from the expanded state to the contracted state, the selected distance being commensurate with a desired level of tightening of the orthotic device about the patient's chest to limit the expansion of the surgically repaired split sternum thereby minimizing the chest pain in the patient's chest.

* * * * *